United States Patent [19]

Login et al.

[11] Patent Number: 4,994,237
[45] Date of Patent: Feb. 19, 1991

[54] MICROWAVE PRESERVATION OF BIOPROSTHESES

[75] Inventors: Gary R. Login; Robert G. Johnson, both of Brookline; Ann M. Dvorak, Newton Center, all of Mass.

[73] Assignee: The Beth Israel Hospital Association, Boston, Mass.

[21] Appl. No.: 435,332

[22] Filed: Nov. 13, 1989

Related U.S. Application Data

[63] Continuation-in-part of Ser. No. 104,631, Oct. 2, 1987, abandoned.

[51] Int. Cl.$^5$ .......................... A61L 2/12; A01N 1/02
[52] U.S. Cl. ........................................ 422/21; 422/36; 422/37; 422/40; 435/1
[58] Field of Search ...................... 422/21, 36, 37, 40; 435/1

[56] References Cited

U.S. PATENT DOCUMENTS

| | | |
|---|---|---|
| 1,602,489 | 10/1926 | Hochstetter et al. |
| 3,479,196 | 11/1969 | Heimann |
| 3,645,849 | 2/1972 | Gray |
| 3,743,480 | 7/1973 | Falk |
| 4,351,091 | 9/1982 | Goodkin |

FOREIGN PATENT DOCUMENTS

| | | |
|---|---|---|
| 84/01894 | 5/1984 | PCT Int'l Appl. |
| 0651815 | 3/1979 | U.S.S.R. |

OTHER PUBLICATIONS

Login et al., Lab. Invest., 57:592, (1987).
Login et al., Lab. Invest., 57:585, (1987).
Leong, Pathol. Annual, 23:213-233, (1988).
Boon et al., Histochemical Journal, 20:313-322, (1988).
Sabatini et al., J. Cell Biology, 17:19, (1983).
Steinmetz et al., J. Thoracic and Cardiovas. Surg., 47:186, (1964).
Pritchard et al., J. Thoracic and Cardiovas. Surg., 52:232, (1966).
Harris et al., Surgery, 63:45, (1968).
Mayers, J. Clin. Path., 1969, p. 273.
Robertson et al., J. Ultrastructure Research, 30:275, (1970).
Zimmerman et al., Laboratory Medicine, 1972, p. 29.
Bernard, Stain Technology, 49:215, (1974).
Gordon et al., Am. J. Med. Tech., 40:441, (1974).
Tan et al., Ann. Thoracic Surg., 22:188, (1976).
Wakabayashi et al., J. Hist. Cytochem., 23:632, (1975).
Burke et al., Human Lab Science, 13:267, (1976).
Petrere et al., Stain Technology, 52:113, (1977).
Mufson et al., J. Invest. Derm., 69:547, (1977).
Spray et al., Am. J. Cardiology, 40:319, (1977).
Latimer et al., J. Clin. Microbiology, 6:340, (1977).
Login, Am. J. Med. Tech., 44:435, (1978).
Ferrans et al., Am. J. Cardiology, 41:1159, (1978).
Jones et al., Neuropharmacology of Cyclic Nucleotides, 253, (1979).
Broom et al., Thorax, 34:166, (1979).
Patterson et al., Stain Tech., 55:71, (1980).
Barry et al., 38th Ann. Proc. Elec. Micro. Soc. of Am., 516, (1980).
Ellis et al., Microwave Fixation Workshop, (1980).
Riddle et al., J. Thoracic Cardio. Surg., 81:279, (1981).
Marvyama, Trends in Pharmaceutical Sci., p. 239, (1981).
Science, 222:895, (1983).
Levy et al., A.J.P., 113:143, (1983).
Brinn, J. Histotech, 6:125, (1983).
Chew, Cell Biology, p. 135, (1983).
Hopwood et al., p. 1711, (1984).
Fox et al., J. Histochem. Cytochem., 33:845, (1985).
Estrada et al., Am. J. Clin. Path., 83:639, (1985).
Hafiz et al., J. Clin. Pathol., 38:1073, (1985).
Leong et al., J. Pathol., 146:313, (1985).
Boon et al., Histopathol., 10:303, (1986).
Leong et al., J. Pathol., 148:183, (1986).
Rohrer, 101:49, Am. J. Ophthalmology, (1986).
Levy et al., AJP, 122:71, (1986).
Ademic et al., Ann. Meeting, Abstracts, 54:73A, (1986).
Mead et al., Am. J. Clin. Pathol., 85:510, (1986).
Login et al., Am. J. Pathol., 120:230, (1985).
Login et al., J. Histochem. Cytochem., 34:381, (1986).

Primary Examiner—Robert J. Warden
Assistant Examiner—Jill Johnston
Attorney, Agent, or Firm—Lorusso & Loud

[57] ABSTRACT

A method to preserve and sterilize biological tissues by exposing the tissue to microwave irradiation, thereby limiting tissue exposure to standard organic preservatives and retaining tissue pliability and other qualities that characterize natural, unpreserved tissue.

14 Claims, 2 Drawing Sheets

MICROWAVE PRESERVATION OF BIOPROSTHESES

CROSS REFERENCE TO RELATED APPLICATION

This application is a continuation-in-part application of application to Gary R. Login et al., entitled "Microwave Preservation of Bioprosthesis", U.S. Ser. No. 07/104,631, filed Oct. 2, 1987, now abandoned.

BACKGROUND OF THE INVENTION

1. Field of the Invention

This invention relates to a method to prepare biological tissues (e.g. heart valves, veins, cartilage, ligaments) and organs for use as bioprostheses, and more particularly, it relates to a rapid method to preserve tissue samples with a solution, to irradiate samples in a microwave oven, and to store samples in a storage medium.

2. Prior Art

One of the earliest examples of replacement tissue (otherwise known as a bioprosthesis) is the porcine valve which was used to replace defective human heart valves. Before any bioprosthesis is implanted, it must be treated with disinfectants and preservatives (such as chemical, x-ray, or cold treatments) to prevent infection and to maintain the structural integrity of the bioprosthesis. If a bioprosthesis were not treated with preservatives, it would degenerate following implantation and fail to function. In the early stages of this technology, bioprostheses were prepared by immersion in a formaldehyde solution prior to implantation. Using this tanning technology, valves fail to mechanically function properly because the formaldehyde predisposes the valve to either tears in or calcific deposits on the valve leaflets. Levy et al. *Am. J. Pathol.*, 113:143 (1983). The literature teaches that aldehydes are responsible for the mechanical failure of the valve leaflet. The literature currently promotes the use of glutaraldehyde in place of formaldehyde. Furthermore, the literature suggests that reducing the exposure time of the bioprosthesis to the glutaraldehyde or formaldehyde and/or reducing the aldehyde concentration (using conventional tanning methods) would have a limited effect in eliminating mechanical valve failure. Levy et al., *Am. J. Pathol.*, 122:71 (1986).

An effective method of valve sterilization and storage would be one which causes minimal structural change to the collagen and elastic components of the biological tissue. Tan et al., *Annals of Thoracic Surg.*, 22:188 (1976). Collagen is a fibrous protein which gives tissues their structural integrity and makes the tissues resistant to tearing. Collagen fibers form an extracellular framework around tissue cells. Aldehydes induce covalent cross-linking, making collagen fibers rigid as the number of covalent cross-linkages increases.

Aldehydes, as a class, are effective antimicrobial agents, Burke et al., *Human Lab Science*, 13:267 (1976), which combine a number of organic functional groups on proteins ($-NH_2$, OH, $-COOH$, and SH). Spontaneous reactions with the amino groups of proteins leads to protein inactivation by forming methylene-bridged cross-links between amino groups. Sterilization and disinfecting applications of formaldehyde and glutaraldehyde are limited by their slow action (hours) and their uncontrollable reaction rate. Id. In addition, exposure to aldehyde on the order of hours results in irritation of lab workers' respiratory tracts. *Science*, 222:895 (1983). Prolonged aldehyde immersion is suspected to be responsible for the hardening of collagen, causing tissue to become brittle. Tissue breaks, tears, and calcification are all direct consequences of brittleness. Ferrans et al., *Am. J. Cardiology*, 41:1159 (1978); Spray et al., *Am. J. Cardiology*, 40:319 (1977); Tan et al., *Ann. Thoracic Surg.*, 22:188 (1976).

In the field of immunology, low concentrations of glutaraldehyde (0.02% to 0.1%) are used to preserve tissue antigens for immunohistochemical studies. (As used throughout the specification and claims, all percentages are by weight, unless otherwise stated.) Preservation protocols for antigens and enzymes result in poor preservation of the structural integrity of the tissue since these same gentle preservation protocols do not induce a sufficient level of cross-linking. Sabatini et al. *J. Cell Biology*, 17:19 (1963); Robertson et al., *J. Ultrastruct. Research*, 30:275 (1970); Wakabayashi et al., *J. Histochem. Cytochem.*, 23:632 (1975).

Preparing tissues by present tanning methods requires long exposure times (hours to months) to moderate glutaraldehyde concentrations (0.625% to 5%). The long exposure time to glutaraldehyde is thought to be necessary for complete penetration of the tissue as well as for tissue sterilization. Mechanical failure, secondary to altered collagen, results in the leading cause of heart valve failure even with glutaraldehyde concentrations as low as 0.625% and with exposure as brief as 24 hours. Broom et al., *Thorax*, 34:166 (1979).

In the field of histology, the study of tissue structure, the object is to fix cells by preserving their intra- and extracellular architecture. Since the diffusion of glutaraldehyde into tissues is slow (on the order of hours), fixation procedures usually entail long exposure times of tissue specimens to high aldehyde concentrations. This results in very brittle tissue. Glutaraldehyde (in concentrations of 2% to 4%) is used under certain circumstances in histology (e.g. electron microscopy); formaldehyde (in a 4% concentration) is routinely used (e.g. in light microscopy). The goal of fixation is to preserve all cell types and products, not just collagen. That is, histological procedures preserve many cell types and products at the expense of cross-linking collagen, making it shrink and become rigid. Fox et al., *J. Histochem. Cytochem.*, 33:845 (1985). In fact, Ferrans et al. specifically teach that "the concentration of glutaraldehyde used in either the Hancock or in the Carpentier-Edwards process is not sufficiently great to produce tissue fixation of a quality comparable with that needed for ultrastructural study." Ferrans et al., supra.

Recent improvements in the field of histology include the use of microwave energy fixation of surgical specimens for light and electron microscopy. The purpose of the microwave step in fixing specimens is to accelerate the reaction of aldehyde cross-linking with proteins. Boon et al., *Histochem J.*, 20:313 (1988). In this histological procedure, biological specimens are first exposed to solutions of 2-4% formaldehyde and/or glutaraldehyde (typically one hour) prior to microwave heating the solution to temperatures between 50° and 68° C. Leong, *Pathology Annual, Part 2*, 23:213 (1988); Boon et al., supra. A final microwave fixation temperature of 50° C. or lower is specifically taught against because of the ". . . reduction in brilliance of staining with hematoxylin and eosin." Leong et al., *J. Pathol.*, 146:313 (1985). Then routine tissue processing, paraffin embedding, and staining procedures are performed. Raising the temperature of the specimen and aldehyde using conventional heating sources results in increasing the rate of cell autolysis more so than increasing the rate of diffusion of aldehyde into the specimen. The use of microwave energy in histology is simply a faster method for preparing histological specimens with no other known or reported inherent advantages.

Generally, tissue specimens which are preserved by means of standard tanning processes incorporating glutaraldehyde tend to tear, calcify, and develop thrombi within 4 to 7 years. Riddle et al., *J. Thor. Cardiovasc. Surg.*, 81:279 (1981). Tearing of the bioprosthesis results from repeated flexing of the collagen, made rigid by aldehydes. Calcification is a condition whereby calcium salts from the bloodstream form deposits on stressed or damaged tissues. These deposits develop into hard obstructions within a patient's body, particularly on valve leaflets. A thrombus is a blood clot which is formed at a site of damage to the delicate, internal lining of blood vessels or the heart. Blood clot formation can be triggered by rough surfaces, such as calcified leaflets or tears in the endothelial lining, which cause platelets to release potent clotting factors permitting formation of fibrin fibers which trap red blood cells (erythrocytes) thereby decreasing the function of the leaflets.

The drawbacks to the standard method of using glutaraldehyde to preserve valves are that it induces rigidity in the tissue, making it susceptible to tears in the valves, calcification of the valve leaflets, and induces thrombi following implantation. Leaflets which are less pliable or flexible than natural in vivo valves have poor physiologic function. Current glutaraldehyde preservation techniques require hours to days. Excessive cross-linking and rigidity of collagen in the valve, secondary to prolonged aldehyde exposure time, is considered responsible for the subsequent mechanical failure. Tan et al., supra. The prolonged processing time makes quality control difficult. By storing the valves in a glutaraldehyde solution, an indeterminate amount of additional valve rigidity results as well. Sherman et al., *Trans. Am. Soc. Artif. Intern Organs*, 30:577 (1984) state that "'control of the extent of cross-linking may represent, therefore, one possible approach to limiting eventual calcification."

SUMMARY OF THE INVENTION

In accordance with the present invention, it has been discovered that microwave irradiation in conjunction with a physiologic salt solution or a dilute aldehyde solution, leads to a degree of preservation such that tissue flexibility is promoted and collagen cross-linking is minimized.

Accordingly, the present invention is a method to provide bioprostheses for implantation into patients. Within seconds to minutes after the tissue is removed from its blood supply, it is immersed in an osmotically balanced solution (OBS) defined subsequently. The immersed tissue is then irradiated in a microwave oven for seconds until the OBS reaches a temperature within the range of 35° C. to 50° C. As soon as possible and preferably within thirty seconds after irradiation, the tissue is transferred and stored in a cold sterile saline solution. By following the procedure of the present invention, long exposure time to glutaraldehyde and formaldehyde is limited and/or eliminated. The bioprostheses produced by the present invention retain their pliability and other qualities that characterize natural, unpreserved tissue.

It is therefore an object of the present invention to provide an improved method to preserve bioprostheses for implantation into patients whereby the tissue retains many characteristics of the living tissue.

It is an object of the present invention to provide bioprostheses which exhibit better mechanical properties than prior bioprostheses.

It is another object of the present invention to provide bioprostheses for implantation into patients which decrease the ischemic time interval for structural and histological preservation.

It is a further object of the present invention to provide a method to rapidly prepare bioprostheses.

It is yet another object of the present invention to provide bioprostheses for implantation into patients which minimize or eliminate the specimens exposure to glutaraldehyde and formaldehyde.

DESCRIPTION OF THE PREFERRED EMBODIMENTS

At the outset, the invention is described in its broadest overall aspects with a more detailed description following. The broadest aspects of the invention involve removing the tissue from its blood supply, immersing the tissue in an osmotically balanced solution (OBS) initially at room temperature (approximatly 20° C.), irradiating the immersed tissue with microwave energy at a sufficient dose and for a sufficient time such that the temperature of the solution is within the range of 35° C. to 50° C., and storing the tissue in a sterile OBS until it is implanted in a patient.

Figure 1:
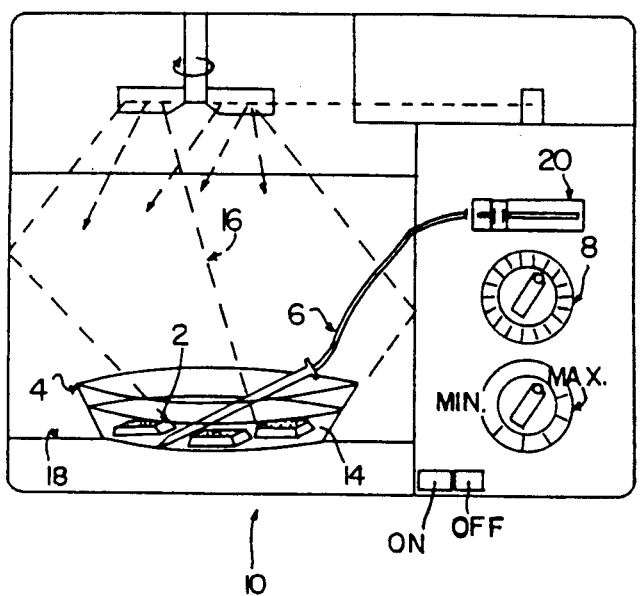
FIG. 1 is a schematic diagram for the procedure of the present invention showing the tissue in a microwave oven.

As shown in FIG. 1 of the drawing, a glass tray 4 centered on the glass platform of the microwave oven 18 and filled with solution 14 to a maximum height (depth) of 1 cm. The microwave temperature probe 6 is immersed in the solution 14 and the oven shut-off temperature is pre-set within the 35° to 50° C. range. (Beyond this range, the important physiologic characteristics of collagen will be altered.) The tissue specimens 2 are submerged in the OBS 14. The power indicator on the oven 12 is set at maximum or high. Setting the timer on the oven 8 is irrelevant since the extent of the treatment is determined on the basis of the solution temperature. The oven 10 is turned on and the tissue specimens 2 are subjected to microwaves 16. The microwave energy is supplied by the oven 10 which is either a standard microwave oven or a specially designed microwave oven which further reduces the aldehyde exposure time. The duration of the microwave treatment is determined by the temperature of the solution 14, thus the microwave oven 10 will automatically shut off when the pre-set final irradiation temperature of the solution is obtained. The tissue specimens 2 are removed from the warm solution and stored in a cold sterile saline solution or OBS as soon as possible and preferably within thirty seconds of irradiation. The OBS used for storage of the tissue specimens 2 may contain 0.001%–0.1% glutaraldehyde, a calcium chelating agent such as 1–100 mM ethylenediaminetetraacetic acid (EDTA), 0.02% sodium azide (or other inhibitor of microbial growth such as 0.02% thimerosal), or some combination of these elements.

Osmotically balanced solutions (OBS) are utilized to prevent the loss of important cellular constituents due to diffusion. The solution 14 in which the tissue specimens are immersed is one of the following room temperature OBS: a physiologic saline solution (0.9% sodium chloride), a phosphate buffered saline solution (PBS) consisting of 0.87% sodium chloride, 0.12% sodium phosphate dibasic, and 0.015% sodium phosphate monobasic, a solution of 25 mM N-2-hydroxyethylpiperazine-N$^1$-2-ethanesulfonic acid (HEPES), or a solution of 20 mM Tris(hydroxymethyl)aminomethane and 0.9% sodium chloride, pH 7.3–7.6 (TRIS). Each of these solutions may also contain 0.001–0.1% glutaraldehyde or a calcium chelator such as 1–100 mM EDTA, or both. Table 1 illustrates the optimal conditions under which these different solutions may be used. Water is the solvent for all solutions.

proteins. This is unlike conventional heating in an oven which results in a temperature gradient from the outside to the inside of the specimen. Microwaves also induce an electromagnetic field in the biological specimen, which is postulated to stop cell function by rearranging highly oriented molecular assemblies. Cleary, *Department of Health, Education, and Welfare* (FDA), 78-8055:1, 1978. Microwave irradiation is also known to destroy viruses and bacteria, and, thus, sterilize the tissue. Rohrer et al., *Am. J. Opthalmology*, 101:49 (1986); Latimer et al., *J. Clin. Microbiology*, 6:340 (1977). The present invention uses microwave energy in combination with an aldehyde at a concentration below that which is used to preserve cells for histology. In addition, calcium salts which are in aldehyde fixatives and which are necessary to maintain cell integrity for electron microscopy are omitted in OBS used in microwave preservation of bioprostheses to further prevent calcification.

STUDY I

A comparison study of the treatment of bioprostheses was conducted with pig valves. Valve leaflets were dissected from pigs under surgically clean conditions within fifteen minutes after the cessation of blood flow. Within fifteen minutes after harvesting, the valve leaf-

TABLE 1

| Microwave Solution | Sample Solution Composition (solvent = H$_2$O) | Irradiation Time | Final Solution Temperature |
|---|---|---|---|
| physiologic saline | 0.9% sodium chloride | 1–50 s | 35°–50° C. |
| PBS | 0.87% sodium chloride, 0.12% sodium phospate dibasic and 0.015% sodium phosphate monobasic | 1–50 s | 35°–50° C. |
| HEPES | 25 mM HEPES | 1–50 s | 35°–50° C. |
| TRIS | 20 mM Tris and 0.9% sodium chloride | 1–50 s | 35°–50° C. |
| buffered calcium chelator | 1–100 mM EDTA in 0.9% sodium chloride, PBS, HEPES or TRIS | 1–50 s | 35°–50° C. |
| buffered glutaraldehyde mixture | 0.001–0.1% glutaraldehyde in 0.9% sodium chloride, PBS, HEPES or TRIS | 1–50 s | 35°–50° C. |
| buffered calcium chelator and glutaraldehyde mixture | 1–100 mM EDTA plus 0.001–0.1% glutaraldehyde in 0.9% sodium chloride, PBS, HEPES or TRIS | 1–50 s | 35°–50° C. |

As Table 1 shows, the present invention is applicable to known dilute preserving solutions and calcium chelating agents. Aldehydes used in the various preserving solutions have a maximum of 6 carbons and are liquids. All tissue specimens were harvested from donor animals using surgically clean techniques. All tissues treated with microwave energy had either a good pliable feel or appeared less rigid than those tissues treated in the conventional manner (immersion in a Hancock preparation containing 0.6% glutaraldehyde for 24 hours, followed by storage in 0.2% glutaraldehyde for an indefinite time period typically months or years).

The object of the present invention is to preserve biologic tissue for implantation into animals or humans such that the bioprosthesis will function physiologically (i.e. resist mechanical failure under physiologic conditions). In order to achieve this goal, microwave energy is used to irradiate the tissue. Microwaves uniformly penetrate and rotate dipolar molecules millions of times a second, thereby heating specimens uniformly and instantaneously, resulting in controlled coagulation of lets were rinsed in standard electrolyte solution and fixed using three different treatment methods: (a) immersion in a 0.6% glutaraldehyde solution for 24 hours at 25° C. (standard glutaraldehyde treatment, Broom et al., *Thorax*, 34:166 (1979)); (b) immersion in an aldehyde OBS at 22° and exposure to microwave irradiation for 11 seconds to reach a final solution temperature of 47° C.; and (c) immersion in an aldehyde OBS at 22° C. wherein irradiation exposure time was limited to 8 seconds at which time the solution reached a final temperature of 40° C. Microwave treated samples were removed from the warm solution within thirty seconds and were stored in 0.9% saline at 4° C. with 0.02% sodium azide, for a minimum of 24 hours.

The tensile strengths of the valve leaflets were determined in order to quantitate the structural changes following the various valve treatments. Tensile strength testing is an effective means to investigate detrimental effects of valve preservation/treatment on tissues since tensile strength is a "fundamental parameter" of bioprosthetic function. Pritchard et al., *J. Thoracic Cardiovasc. Surg.*, 52:232 (1966). Better methods of preparing bioprostheses should result in leaflets with high tensile strength—ideally commensurate with natural tissue—since such methods are expected to involve "minimal structural change to the collagen and elastic components" of the tissue. Tan et al., *Ann. Thoracic Surg.*, 22:188 (1976).

In order to test tensile strengths, the leaflets were trimmed parallel to the annulus. One 2 mm wide by 1.4 cm long strip of tissue was obtained from each leaflet and trimmed with a thin isthmus, centrally located so as to induce breakage at the isthmus rather than at the clamp. Pritchard et al., *J. Thoracic Cardiovasc. Surg.* 52:232 (1966). The leaflet strips were held by pneumatic clamps with one clamp face serrated and the other rubber-coated. A 0.1 to 0.25 inch gauge length was used in recording the applied tension. A 500 gram test cell was used (Instron model 4201 mechanical testing machine, Canton, Mass.) with 0.2 inch/minute pulling rate. All strips were tested "wet" (bathed with 0.9% saline solution.)

Figure 2:
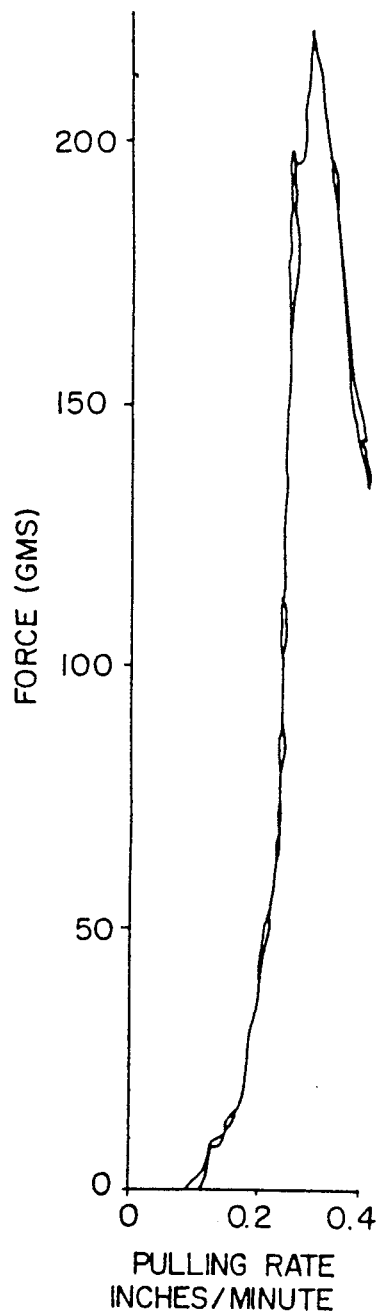
FIG. 2 is a graph illustrating the ultimate tensile strength of tissue prepared using the "standard glutaraldehyde" treatment.
Figure 3:
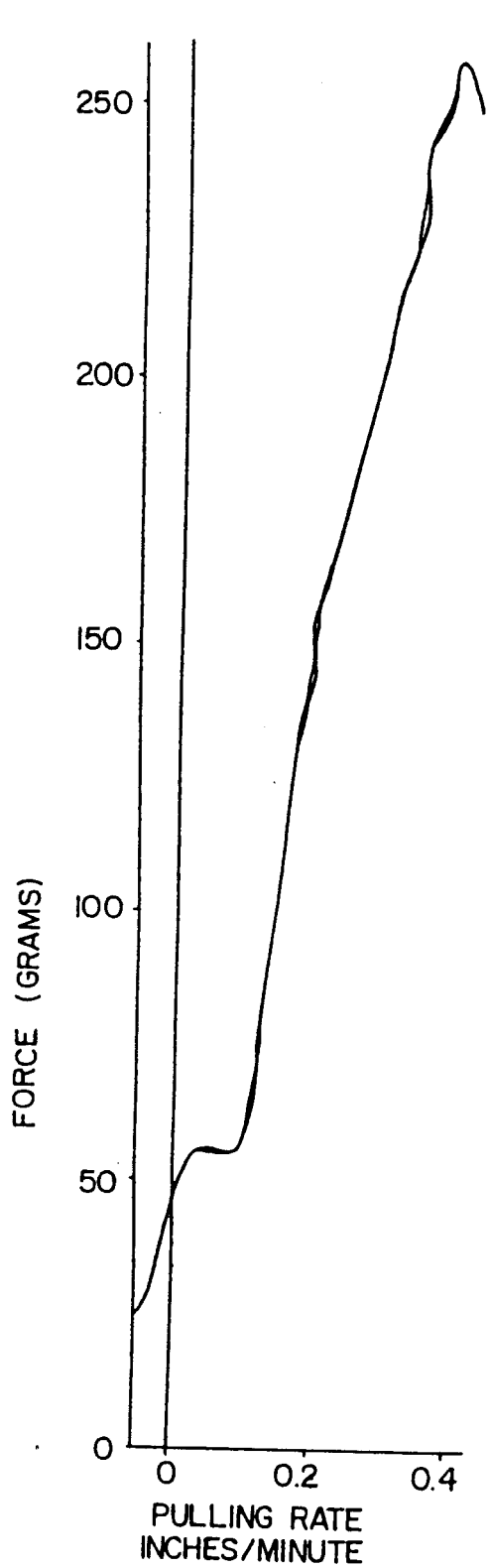
FIG. 3 is a graph illustrating the ultimate tensile strength of tissue prepared using the method of the present invention at "high temperature"
Figure 4:
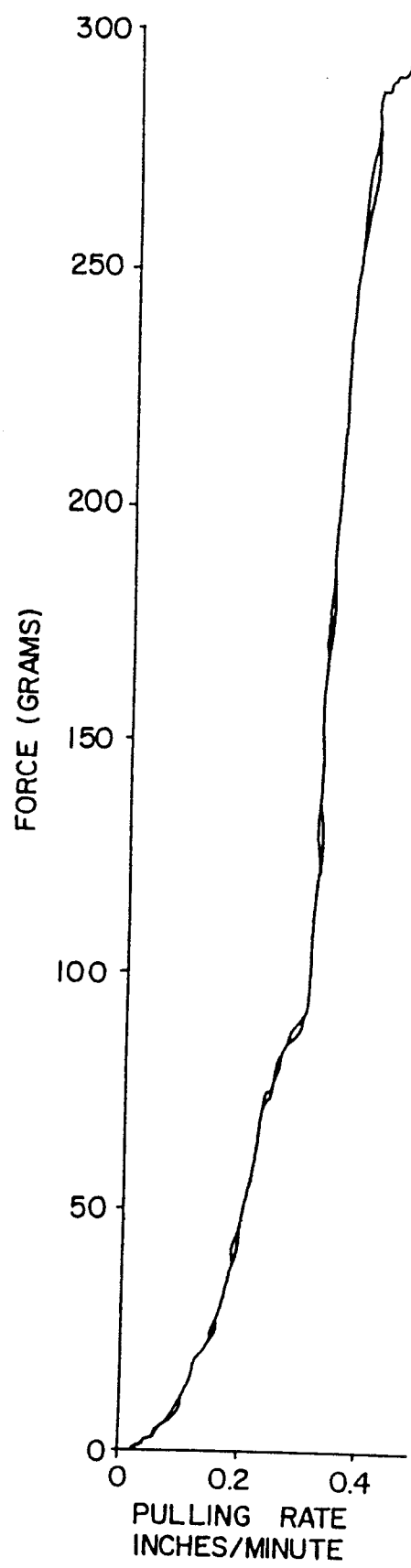
FIG. 4 is a graph illustrating the ultimate tensile strength of tissue prepared using the method of the present invention at "low temperature."

Referring to FIGS. 2, 3 and 4, the peak on the curve represents the rupture or ultimate tensile strength of the tissue. The rupture point of the "standard glutaraldehyde" treated tissue was 220 grams and is shown in FIG. 2. The rupture point of the "high temperature" microwave treated leaflet, FIG. 3, was 260 grams which is an 18% increase in the ultimate tensile strength compared to the "standard glutaraldehyde" treated valve. The leaflet treated with "low temperature" microwave irradiation, FIG. 4, exhibited a 34% increase in the ultimate tensile strength compared to the "standard glutaraldehyde" treated valve. Its breaking point was 295 grams. Thus, microwave treatment of bioprostheses reduces the preparation time and maintains higher tensile strength of the tissue than conventional valve tanning methods. Our results are in agreement with the literature which states that chemical agents which alter the structure of collagen yield a "striking" 35% reduction in tensile strength compared to fresh, unfixed, tissue controls. Harris et al., *Surgery*, 63:45 (1968). Our results indicate that the microwave method in accordance with the present invention, better approximates the ultimate tensile strength characteristics of the living tissue.

STUDY II

In a second comparison study, pig valve leaflets were exposed to a variety of osmotically balanced solutions and microwave conditions, and evaluated for calcification following implantation into rats. Leaflets were harvested as previously reported in Study I and immersed in the following solutions initially at room temperature: (a) 0.1-0.5% glutaraldehyde in PBS, and (b) 0.1-2.5% glutaraldehyde plus 2.0% formaldehyde plus 0.025% calcium chloride in 0.1 M sodium cacodylate buffer (a standard fixative formulation for electron microscopy). The leaflets were exposed to microwave energy for 5-8 seconds as soon as possible and preferably within fifteen minutes after immersion in solution (a) or (b). The final solution temperature ranged between 36° C. and 47° C. Leaflets were rinsed in room temperature 0.9% sodium chloride and implanted subcutaneously in surgically prepared pouches along the abdominal wall of 3 week old, phenobarbital anesthetized rats. The rats were sacrificed 3 weeks following implantation, and ten leaflets were harvested, fixed in 10% formalin and processed to paraffin blocks. Sections 4 microns thick were stained with hematoxylin and eosin and examined by light microscopy.

The results showed that more than 75% of the leaflets do not calcify when they are microwave irradiated in PBS containing 0.1% glutaraldehyde. However, almost all leaflets exposed to 0.5% or greater glutaraldehyde and/or formaldehyde do calcify regardless of microwave exposure. The current literature teaches that conventional methods of brief exposure of collagen-containing implants to as little as 0.1% glutaraldehyde will result in pathologic calcification (Levy et al., *Am. J. Clinical Pathology*, 122:71 (1986)).

STUDY III

In a third comparison study we evaluated the leaflets for microbiological contamination secondary to our handling procedures or the presence of endogenous organisms (e.g. mycobacterium). Pig leaflets were harvested under surgically "clean" conditions described in Study I and exposed to osmotically balanced solutions listed in Study II. Small portions of the leaflets used in the implantation stud (Study II) were placed in labeled transport vials containing sterile saline. The samples were aseptically fragmented and incubated in media to evaluate aerobic growth (3 days), anaerobic growth (6 days), and mycobacterium (2 months). Identification of cultured organisms was accomplished by gram stain and selective media.

Bacterial growth occurred in 3 out of 27 tests (twice in unfixed samples and once in a microwave condition). The Staphylococcus and Enterococcus contaminants were most likely due to handling. Mycobacterium was not isolated.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalents thereof. Hence, it is recognized that various modifications are possible when within the scope of the present invention as claimed.

What is claimed is:

1. A method to preserve and sterilize bioprostheses comprising the following steps:
   immersing a specimen of biologic tissue in a preserving solution at room temperature (20° C.) selected from a member of the group consisting of:
   (a) 0.9% sodium chloride;
   (b) 0.87% sodium chloride, 0.12% sodium phosphate dibasic, and 0.015% sodium phosphate monobasic, pH 7.3-7.6 (PBS);
   (c) 20 mM Tris(hydroxymethyl)aminomethane and 0.9% sodium chloride, pH 7.3-7.6 (TRIS);
   (d) 25 mM N-2-hydroxyethylpiperazine-N¹-2-ethanesulfonic acid, pH 7.3-7.6 (HEPES);
   (e) 0.001-0.1% glutaraldehyde in a solution selected from a member of the group consisting of (1) 0.9% sodium chloride, (2) PBS, (3) HEPES, and (4) TRIS;
   (f) a calcium chelating agent in a solution selected from a member of the group consisting of (1) 0.9% sodium chloride, (2) PBS, (3) HEPES, and (4) TRIS; and
   (g) a calcium chelating agent and 0.001-0.1% glutaraldehyde in a solution selected from a member of the group consisting of (1) 0.9% sodium chloride, (2) PBS, (3) HEPES, and (4) TRIS;

exposing the immersed specimen to microwave irradiation until the final temperature of the solution is between 35° and 50° C.; and, storing the irradiated specimen in a cold sterile osmotically balanced solution selected from the group consisting of (1) 0.9% sodium chloride, (2) PBS, (3) HEPES, and (4) TRIS.

2. The method to preserve and sterilize bioprostheses as set forth in claim 1 wherein said biologic tissue is immersed in the osmotically balanced preserving solution within fifteen minutes after it is harvested from a donor animal and exposed to microwave irradiation.

3. The method to preserve and sterilize bioprostheses as set forth in claim 1 wherein said preserving solution is osmotically balanced to said biologic tissue.

4. The method to preserve and sterilize bioprostheses as set forth in claim 1 wherein said preserving solution is 1-100 mM of the calcium chelating agent ethylinediamenetetraacetic acid (EDTA) in a solution selected from the group consisting of (1) 0.9% sodium chloride, (2) PBS, (3) HEPES, and (4) TRIS.

5. The method to preserve and sterilize as set forth in claim 1 wherein said preserving solution is 1-100 mM of the calcium chelating agent EDTA and 0.001-0.1% glutaraldyde in a solution selected from the group consisting of (1) 0.9% sodium chloride, (2) PBS, (3) HEPES and (4) TRIS.

6. The method to preserve and sterilize bioprostheses as set forth in claim 1 wherein said biologic tissue is irradiated in a microwave oven for between one and fifty seconds until the solution reaches a temperature in the range of 35° to 50° C.

7. The method to preserve and sterilize bioprostheses as set forth in claim 1 wherein said cold sterile osmotically balanced storage solution has a temperature of 4° C.

8. The method to preserve and sterilize bioprostheses as set forth in claim 1 wherein said cold sterile osmotically balanced storage solution further comprises an inhibitor of microbial growth.

9. The method to preserve and sterilize bioprostheses as set forth in claim 8 wherein said inhibitor of microbial growth is selected from the group consisting of 0.02% sodium azide and 0.02% thimerosal.

10. The method to preserve and sterilize bioprostheses as set forth in claim 1 wherein said cold sterile osmotically balanced storage solution further comprises a calcium chelating agent.

11. The method to preserve and sterilize bioprostheses as set forth in claim 10 wherein said calcium chelating agent is 1-100 mM EDTA.

12. The method to preserve and sterilize bioprostheses as set forth in claim 1 wherein said cold sterile osmotically balanced storage solution further comprises 0.001-0.1% glutaraldehyde.

13. A method to preserve and sterilize bioprostheses comprising the following steps:

harvesting a specimen of biologic tissue within fifteen minutes after sacrificing a donor animal;

immersing said specimen of biologic tissue within fifteen minutes of harvesting in a room temperature an osmotically balanced solution selected from the group consisting of:

(a) 0.9% sodium chloride;

(b) PBS;

(c) TRIS;

(d) HEPES;

(e) 0.001-0.1% glutaraldehyde in a solution selected from the group consisting of (1) 0.9% sodium chloride, (2) PBS, (3) HEPES, and (4) TRIS;

(f) 1-100 mM EDTA in a solution selected from group consisting of (1) 0.9% sodium chloride, (2) PBS, (3) HEPES, and (4) TRIS;

(g) 1-100 mM EDTA and 0.001-0.1% glutaraldehyde in a solution selected from the group consisting of (1) 0.9% sodium chloride, (2) PBS, (3) HEPES, and (4) TRIS;

exposing the immersed specimen to microwave irradiation within fifteen minutes of immersion in said preserving solution for 1-50 seconds until the temperature of the solution is between 35° and 50° C.; and, storing the irradiated specimen within thirty seconds of irradiation at 4° C. in a sterile osmotically balanced solution selected from the group consisting of (1) 0.9% sodium chloride, (2) PBS, (3) HEPES, and (4) TRIS.

14. The method to preserve and sterilize bioprostheses as set forth in claim 13 wherein said sterile osmotically balanced solution further comprises 1-100 mM EDTA, 0.001-0.1% glutaraldehyde, and an inhibitor of microbial growth selected from the group consisting of 0.02% sodium azide and 0.02% thimerosal.

* * * * *